(12) United States Patent
Campin et al.

(10) Patent No.: US 11,259,916 B2
(45) Date of Patent: Mar. 1, 2022

(54) SYSTEMS AND METHODS FOR MEASURING CILIARY MUSCLE ACTIVITY

(71) Applicant: Alcon Inc., Fribourg (CH)

(72) Inventors: John Campin, Southlake, TX (US); Kevin Liedel, Colleyville, TX (US); George Hunter Pettit, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 173 days.

(21) Appl. No.: 16/161,130

(22) Filed: Oct. 16, 2018

(65) Prior Publication Data

US 2019/0110888 A1   Apr. 18, 2019

Related U.S. Application Data

(60) Provisional application No. 62/573,186, filed on Oct. 17, 2017.

(51) Int. Cl.

| | |
|---|---|
| *A61B 3/00* | (2006.01) |
| *A61B 3/10* | (2006.01) |
| *A61B 3/14* | (2006.01) |
| *A61F 2/16* | (2006.01) |
| *A61B 5/00* | (2006.01) |
| *A61B 5/296* | (2021.01) |
| *A61B 5/389* | (2021.01) |

(Continued)

(52) U.S. Cl.
CPC ............ *A61F 2/1624* (2013.01); *A61B 5/296* (2021.01); *A61B 5/389* (2021.01); *A61B 5/6821* (2013.01); *A61B 5/6844* (2013.01); *A61F 2/16* (2013.01); *A61B 3/10* (2013.01); *A61B 2562/0209* (2013.01); *A61F 2/1637* (2013.01); *A61F 2250/0002* (2013.01); *G02C 7/041* (2013.01); *G02C 7/049* (2013.01); *G02C 7/083* (2013.01)

(58) Field of Classification Search
CPC .. A61B 3/103; A61B 3/08; A61B 3/02; A61B 3/14; A61B 3/113; A61B 3/125; A61B 3/1208; A61B 3/1225; A61B 3/024; A61B 3/1015; A61B 3/107
USPC ....... 351/219, 200, 201–202, 205, 206, 209, 351/210, 220–222, 245, 246
See application file for complete search history.

(56) References Cited

U.S. PATENT DOCUMENTS

| | | |
|---|---|---|
| 9,144,376 B2 | 9/2015 | Guth et al. |
| 9,226,818 B2 | 1/2016 | Campin et al. |

(Continued)

FOREIGN PATENT DOCUMENTS

| | | |
|---|---|---|
| EP | 2687898 A1 | 1/2014 |

OTHER PUBLICATIONS

Alpern, et al., "The electrical response of the human eye in far-to-near accommodation", Arch Ophthal, Oct. 1958, vol. 60:4, pp. 592-602.

(Continued)

*Primary Examiner* — Dawayne Pinkney

(57) ABSTRACT

Systems and methods for non-invasively assessing ciliary muscle accommodative potential in phakic eyes may include receiving a plurality of signals generated by a plurality of bipolar electrodes during a ciliary muscle assessment procedure, each of the plurality of signals indicating an electrical field associated with a patient's ciliary muscle, and analyzing the signals to evaluate the patient's ciliary muscle accommodative potential.

11 Claims, 4 Drawing Sheets

(51) Int. Cl.
    *G02C 7/08* (2006.01)
    *G02C 7/04* (2006.01)

(56) References Cited

U.S. PATENT DOCUMENTS

2014/0371565 A1* 12/2014 Glasser ............... A61B 5/6821
                                                  600/383
2015/0173893 A1   6/2015 Portney
2017/0079771 A1*  3/2017 Roholt ................. G02C 7/083

OTHER PUBLICATIONS

Bornschein, et al., "Bestandpotential und Akkommodationszustand des menschlichen Auges", Graefes Arch Ophthalmol, 1957, vol. 159:2, pp. 45-51.

Hagiwara, "The action potential of the ciliary muscle", Ophthalmologica, 1962, vol. 144, pp. 323-340.

Jacobson, et al., "The electrical activity of the eye during accommodation", Amer J. Ophthal, 1958, vol. 146, pp. 231-238.

Saladin, et al., "Impedance cyclography as an indication of ciliary muscle contraction", Am J. Ophthal, 1974, vol. 51, pp. 613-625.

Schubert, "Aktionspotentiale des M ciliaris beim Menschen", Graefes Arch Ophthalmol, 1958, vol. 157:2, pp. 116-121.

Semmlow, et al., "The relationship between ciliary muscle contraction and accommodative response in the presbyopic eye", Presbyopia Research, Springer Science+Business Media, New York, 1991, pp. 245-253.

Swegmark, "Studies on the electrical impedance of the human eye (a preliminary report)", Acta Ophthalmologica, 1966, vol. 44, pp. 121-131.

Swegmark, "Studies with impedance cyclography on human ocular accommodation at different ages", Acta Ophthalmologica, 1969, vol. 47, pp. 1186-1206.

Swegmark, et al., "Impedance cyclography: a new method for accommodation recording", Acta Ophthalmologica, 1968, vol. 46, pp. 946-968.

* cited by examiner

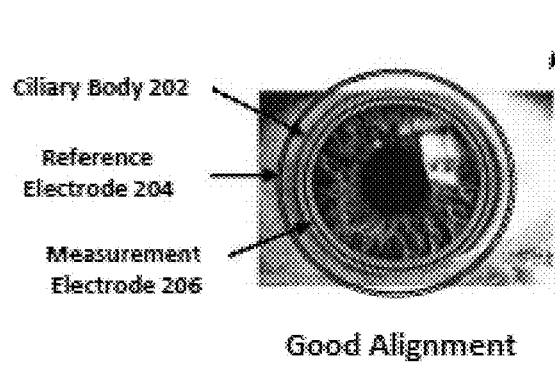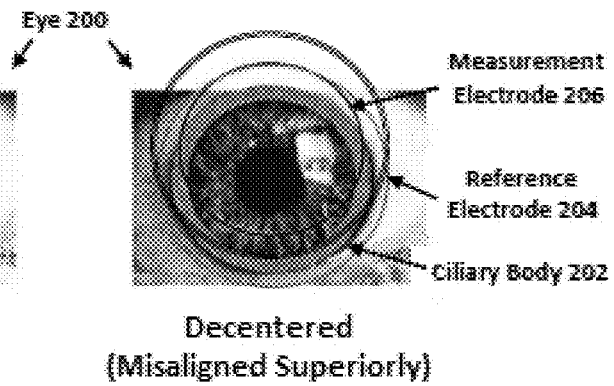
FIG. 2A  FIG. 2B
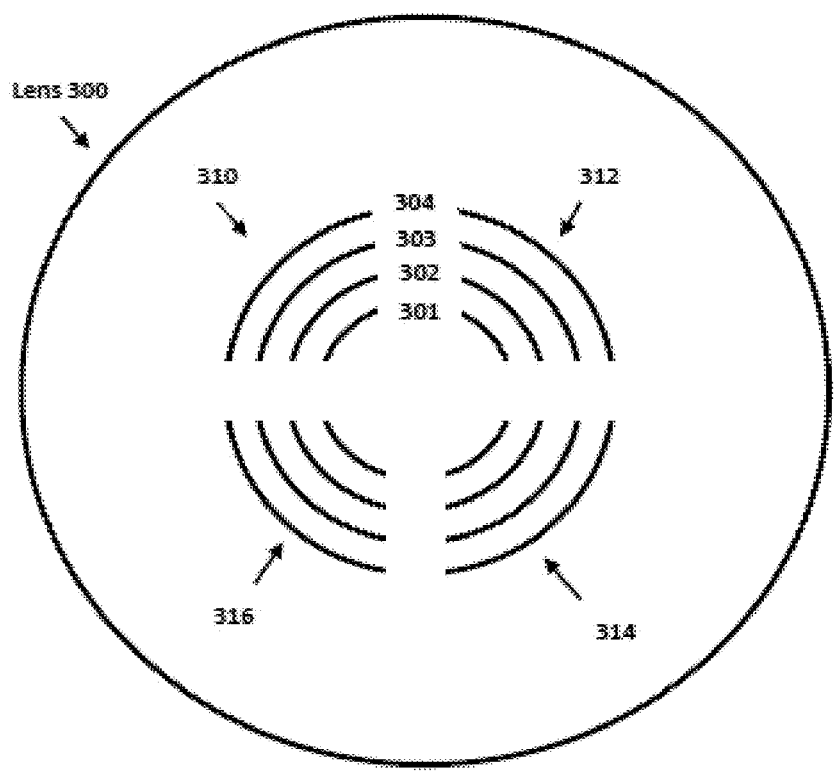
FIG. 3

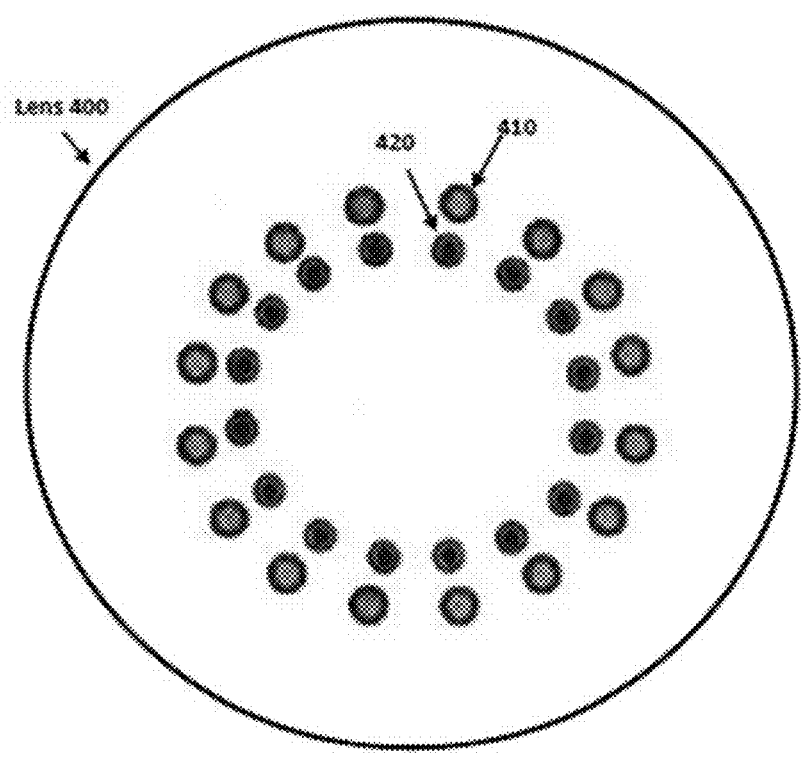
FIG. 4
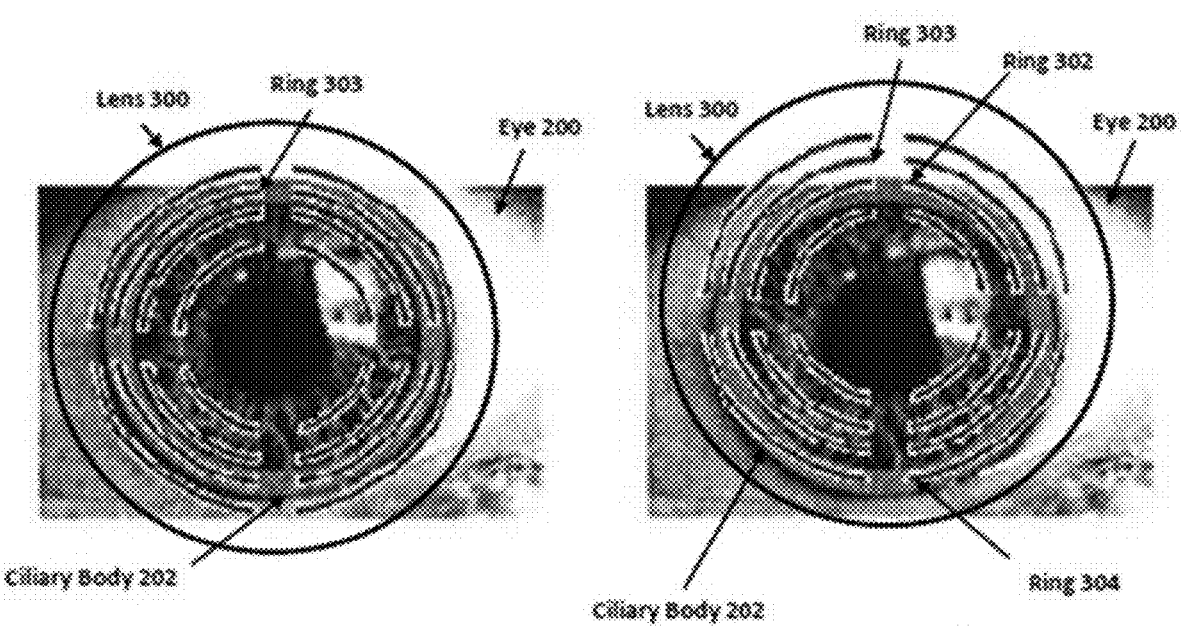
Centered
FIG. 5A
Decentered
(Misaligned Superiorly)
FIG. 5B

SYSTEMS AND METHODS FOR MEASURING CILIARY MUSCLE ACTIVITY

TECHNICAL FIELD

This disclosure relates generally to the field of ophthalmology.

BACKGROUND

The human eye provides vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and ultrasonically vibrated. The vibrating cutting tip liquefies or emulsifies the lens so that the lens may be aspirated out of the eye. The diseased lens, once removed, is replaced by an IOL.

In the natural lens, distance and near vision is provided by a mechanism known as accommodation. The natural lens is contained within the capsular bag and is soft early in life. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change its shape in reaction to the tightening of the ciliary muscle. Furthermore, the ciliary muscle loses flexibility and range of motion. This makes it harder for the lens to focus on near objects, a medical condition known as presbyopia. Presbyopia affects nearly all adults upon reaching the age of 45 to 50. Additionally, patients may also suffer from other conditions, such as age-related macular degeneration (AMD), which may require an even greater degree of magnification to be able to perform visual functions such as reading.

One approach to providing presbyopia correction is the use of an electro-active optical element in an ophthalmic lens, such as an intraocular lens (IOL) or contact lens. Such an electro-active element may be designed to change optical power (and hence the patient's focal distance) in response to action by the ciliary muscle or detection of associated electrical activity. An exemplary approach is disclosed in U.S. Pat. No. 9,226,818 titled SENSORS FOR TRIGGERING ELECTRO-ACTIVE OPHTHALMIC LENSES, which is incorporated by reference herein in its entirety.

In advanced presbyopes, age-related degradation of the muscle may inhibit the ciliary muscle's ability to contract, and the electrical signal attendant to ciliary muscle movement may be attenuated or absent. As a result, there is an inherent risk with accommodative IOLs relying on ciliary muscle-driven action that the muscle may not function, and the IOL may not operate properly. Accordingly, there is a need to determine and characterize electrical activity in the ciliary muscle, and pre-screening procedures are needed to determine whether a patient has the requisite ciliary muscle activity to utilize such an electro-active ophthalmic lens.

SUMMARY

According to certain embodiments, a method includes receiving a plurality of signals generated by a plurality of bipolar electrodes during a ciliary muscle assessment procedure, each of the plurality of signals indicating an electrical field associated with a patient's ciliary muscle and analyzing the signals to evaluate the patient's ciliary muscle accommodative potential. The ciliary muscle assessment procedure may comprise focusing on one or more targets at different distances from the patient. The method may further include providing a contact lens to be applied to a patient's eye, the contact lens comprising the plurality of bipolar electrodes. The at least one of the bipolar electrodes may be aligned with a perimeter of the patient's ciliary muscle when applied to the patient's eye.

In certain examples, analyzing the signals to evaluate the patient's ciliary muscle accommodative potential comprises identifying a subset of the signals corresponding to the at least one of the bipolar electrodes aligned with the perimeter of the patient's ciliary muscle, calculating a value based on the identified subset of signals, and evaluating the patient's ciliary muscle accommodative potential based on the calculated value. Calculating a value based on the identified subset of signals may include calculating a sum of the identified subset of signals. Evaluating the patient's ciliary muscle accommodative potential based on the calculated value may include comparing the calculated sum of the identified subset of signals to a predetermined value.

In certain examples, the plurality of bipolar electrodes comprises plurality of concentric rings, and each concentric ring comprises a plurality of segments. Identifying the subset of the signals corresponding to the at least one of the bipolar electrodes aligned with the perimeter of the patient's ciliary muscle may include identifying at least one signal from a segment of first ring and identifying at least one signal from a segment of a second ring.

In certain embodiments, an ophthalmic system includes a contact lens configured to contact a surface of a patient's eye. The contact lens may include a plurality of bipolar electrodes, each configured to generate a signal indicating an electrical field associated with a patient's ciliary muscle. The system may further include a diagnostic system that includes a processor and memory configured to receive a plurality of signals generated by the plurality of bipolar electrodes during a ciliary muscle assessment procedure, each of the plurality of signals indicating an electrical field associated with a patient's ciliary muscle. The processor and memory of the diagnostic system may be further configured to analyze the received signals to identify a subset of signals which correspond to a subset of bipolar electrodes aligned with the patient's ciliary body, and calculate a value associated with the identified subset of electrodes. The system may further include a display communicatively coupled to the processor and configured to display the calculated value associated with the identified set of electrodes.

In certain examples, the processor and memory of the diatnostic system are configured to analyze the signals to evaluate the patient's ciliary muscle accommodative potential by identifying a subset of the signals corresponding to the at least one of the bipolar electrodes aligned with a perimeter of the patient's ciliary muscle and calculating a value based on the identified subset of signals.

Calculating a value based on the identified subset of signals may include calculating a sum of the identified subset of signals, and the processor and memory of the diagnostic system may be further configured to compare the calculated sum of the identified subset of signals to a predetermined value stored in the memory.

In certain embodiments, the plurality of bipolar electrodes comprises a plurality of concentric rings, and each concentric ring may include a plurality of segments. Identifying the subset of the signals corresponding to the at least one of the bipolar electrodes aligned with the perimeter of the patient's ciliary muscle may include identifying at least one signal from a segment of first ring and identifying at least one signal from a segment of a second ring.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

FIG. 2A depicts an electrode contact lens well-aligned on a patient's eye.

FIG. 2B depicts an electrode contact lens decentered (misaligned superiorly) on a patient's eye.

FIG. 3 illustrates an electrode contact lens, according to certain embodiments.

FIG. 4 illustrates an electrode contact lens, according to certain embodiments.

FIG. 5A depicts an electrode contact lens of FIG. 3 well-aligned on the patient's eye.

FIG. 5B depicts an electrode contact lens of FIG. 3 decentered (misaligned superiorly) on a patient's eye.

Figure 1:
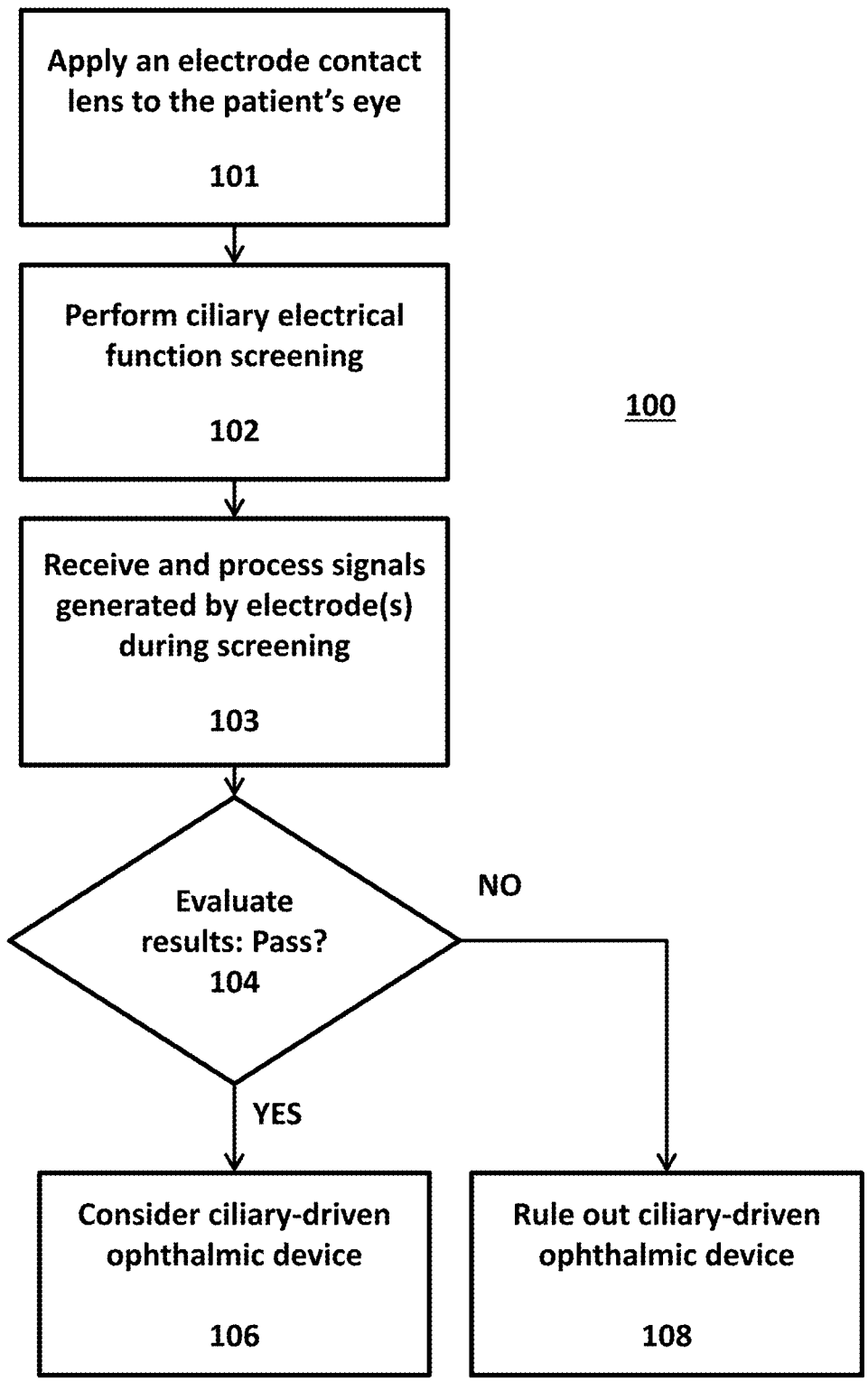
FIG. 1 is a method of evaluating a patient for a ciliary-driven ophthalmic device, according to certain embodiments.

These figures will be better understood by reference to the following detailed description.

DETAILED DESCRIPTION

Efforts are ongoing to develop accommodative IOLs designed to change the power of ophthalmic lenses, such an as IOLs, in response to changes in the ciliary muscle. One sensing technique that has been relatively successful for detecting muscle activity is electromyography. Electromyography is a technique in which the electric field pattern surrounding the muscle is measured over time (such as by electric potential measurements) to determine the degree of muscle contraction. As contrasted with methods such as calcium channel ion detection or other direct detection of the neural signal, electromyography focuses on the electrical activity of the muscle itself, and as such, has proved to be a more reliable gauge of muscle activity. Furthermore, it can provide a continuous indication of the degree of muscle activity, and particularly the degree of force exerted by the muscle, rather than binary detection of a neurological signal.

Movement of a muscle fiber is triggered by depolarization of within the muscle fiber, accompanied by movement of ions, which produces a change in electric field. As the depolarization propagates down the muscle fiber, a biphasic electric field signal is produced that switches signs from positive to negative as the depolarization wave moves along the fiber. Electromyography sensors detect this change in electric field, which allows the muscle activity to be measured. Measurements in skeletal muscle have demonstrated that the intensity varies monotonically and generally linearly with the force exerted by the muscle, so that the electric field can be used as an indicator of the amount of force exerted by the muscle.

In application to ophthalmic lenses and in particular IOLs, the correlation between accommodative demand, the degree to which muscle activity is demanded in response to visual stimuli, and the amount of electrical field in the muscles can be observed for purposes of calibrating the lens. Despite the later ineffectiveness of accommodation due to hardening of the lens and aging of the ciliary muscle and surrounding connective tissue, the ciliary muscle continues to contract even in presbyopic eyes. This can provide an indication of accommodative demand that allows more granular detection than previous sensing techniques, such as detection of neural activity or gross detection of electrical activity as a trigger for accommodation. Consequently, rather than detecting a binary transition between near and far vision, such a system could allow a continuous range of adjustment correlated to the electrical activity of the ciliary muscle tissue, which can in turn be calibrated based on the observed accommodation demand. Such calibration could be based on an average response in the population; alternatively, the calibration could be patient-specific.

U.S. Pat. No. 9,226,818, incorporated by reference herein, discloses exemplary electro-active ophthalmic lenses that include electromyography sensors configured to detect an electric field of a ciliary muscle, generate a signal indicative of the electric field, and adjust optical power for an electro-active optical element based on the signal. In particular embodiments, the sensor provides for automatic control of an electro-active lens. In other embodiments, the sensor provides a user-controlled interface for operating the electro-active lens.

Most accommodative IOLs are designed to change optical power (and hence the patient's focal distance) in response to action by the ciliary muscle. In some cases, performance of such ophthalmic products can be limited due to physiological constraints within the eye, including residual ciliary muscle force. For example, in advanced presbyopes age-related degradation of the ciliary muscle may reduce or possibly eliminate its ability to contract. Without adequate screening, such a patient runs a higher risk of surgically receiving an advanced accommodative IOL which may not work properly after implantation. Accordingly, accommodating IOLs or other ophthalmic devices which work by detecting ciliary muscle electrical activity as an indicator to change optical power may not work effectively if the electrical signal obtained from a patient's ciliary muscle activity is substantially attenuated or absent.

There are currently no techniques available for assessing ciliary muscle accommodative potential in phakic eyes (e.g., prior to removal of the crystalline lens for IOL implantation). Accordingly, embodiments of the present disclosure provide a non-invasive screening technique and tool to preoperatively assess a patient's ciliary electrical activity and evaluate his or her potential to accommodate. This may be accomplished, for example, via sensing of ciliary muscle electrical activity prior to implanting an accommodative IOL or application of custom ciliary muscle-driven accommodating contact lenses, as described herein. Some embodiments may identify eyes in which a ciliary muscle-driven accommodative ophthalmic device would not function as intended, prior to surgery or purchase, to guide the decision on whether such devices are appropriate for a particular individual. While the following description focuses primarily on IOLs, the described techniques could also be used in contact lenses or spectacles driven by ciliary muscle activity.

FIG. 1 is a high-level overview demonstrating a method 100 of screening a patient for a ciliary-driven ophthalmic device, according to certain embodiments. At step 101, a measuring device is applied to a patient's eye. In certain examples, the measuring device comprises an electrode contact lens as described below. The lens may be positioned on the eye such that one or more electrodes in or on the contact lens is adjacent to, on, around, and/or within the ciliary muscle (or a perimeter/circumference thereof) to acquire electrical signal data based on ciliary muscle movement.

At step 102, ciliary function screening is performed. In one example, a care provider may perform a preoperative exam to determine and characterize a patient's ciliary muscle activity. For example, once the electrode contact lens is placed on the eye, the patient may follow instructions to look at objects at varying distances, such as near (e.g., within 40 cm) and far (e.g., beyond 3 m), under an established procedure. As the patient changes focus (or attempts to change focus, as the case may be) to different target distances, the ciliary muscle attempts to change the focusing power of the natural lens accordingly. This causes a change in the electrical field of the patient's ciliary muscle(s) which can be detected and signaled b the electrode(s) on the contact lens.

Accordingly, at step 103, an electrical signal generated by the electrode(s) in response to the electrical field of the ciliary muscle at each distance may be set to and received, processed, and/or recorded by a computer 606 for subsequent presentation and evaluation. In some instances, the electrical signals are transmitted via wired or wireless communication from the electrodes of the lens to the computer 606. As noted below, a plurality of signals may be received from various electrodes on the lens during the screening procedure, and the received signals may be evaluated by the computer 606 (e.g., using summing, averaging, comparing, and/or statistical processing algorithms, etc.) in order to select those which provide the most accurate and/or reliable indication of ciliary muscle activity. The particular electrode signals selected may depend on the position of the contact lens on the patient's eye, as well as the characteristics of the patient's eye itself. The computer 606 may also process the signals and convert them to numerical values or other measurements which characterize ciliary muscle activity, responsiveness, strength, and/or accommodative capacity. Raw or processed signal data may be output by the computer and shown on a display 608.

At step 104, results of step 103 are evaluated. Signal values or measurements generated and/or displayed at step 103 may be reviewed and evaluated by computer 606 and/or a care provider to make a surgical recommendation or choice for the patient (e.g., whether or not to recommend or provide a ciliary-driven accommodative device). Step 104 may be performed manually by a care provider, or automatically by computer 606. For example, the care provider may view and evaluate measurements of ciliary muscle activity generated at step 103 to determine whether they are above or below predetermined threshold(s), or within a predetermined range or target result deemed suitable for utilization of ciliary-driven ophthalmic devices. In other examples, a computer 606 may execute instructions stored in memory to automatically analyze measurements of ciliary muscle activity generated at step 103 and automatically perform such an evaluation. Applicable threshold values, ranges, or targets for comparison may be stored in memory of the computer 606 and may be configured by a user.

If measured ciliary muscle activity generated at step 102 is satisfactory and passes the evaluation at step 104 (e.g., the muscle activity is above a threshold, at a target, or within a predetermined range), the care provider may proceed to step 106. In such cases, ciliary muscle activity may be sufficient to support proper functioning of ciliary-driven ophthalmic devices, such as electro-active accommodative IOLs. The care provider may consider and evaluate ciliary-driven ophthalmic devices when choosing or formulating recommendations for the patient.

If measured ciliary muscle activity generated at step 102 is unsatisfactory and does not pass the evaluation at step 104 (e.g., the muscle activity is below a threshold, far from a target, or outside a predetermined range), the care provider may proceed to step 108. In such cases, ciliary muscle activity may be insufficient to support proper functioning of ciliary-driven ophthalmic devices, such as electro-active accommodative IOLs, and the care provider may consider and evaluate alternatives to ciliary-driven ophthalmic devices when choosing or formulating recommendations for the patient.

Accordingly, certain embodiments of the disclosure provide a technique for non-invasive screening for a ciliary-driven ophthalmic device, including implantable IOLs.

The designs and functionality of the ophthalmic system and electrode contact lens will now be described in additional detail. Various electrode designs for characterizing and measuring ciliary-muscle activity may be developed and used. For example, electrodes for measuring ciliary muscle electrical signals may comprise metal or wire adhered or embedded in a contact lens. Such lenses may be placed on the eye to measure ciliary electrical signals.

In general, the location and spacing of the electrodes relative to the position of the ciliary muscle can have an impact on the ability to detect the electrical signal. For instance, in the case of a continuous electrode (e.g., 360 degrees around an optical axis of a contact lens), as the electrode position is decentered (e.g., misaligned superiorly, as shown in FIGS. 3B and 5B) or moves on the eye (potentially due to gravity, eye movement, or blinking), the signal may be degraded or potentially inverted as the electrode moves off the muscle position. One approach to minimizing the effect of lens movement is to suction the lens onto the corneal surface. However, this can be uncomfortable and may not be entirely effective. Further, such an approach may not address potential signal changes related to ciliary muscle movement.

Another factor which can impact the ability to measure ciliary electrical signal changes is a potential mismatch between the diameter of the ciliary muscle and the diameter(s) of the electrode(s). Indeed, even inter-patient variations in ciliary muscle diameter can be present. Moreover, this can be a static problem or could vary as a function of accommodation if the ciliary muscle contracts appreciably.

To address these and other potential difficulties with accurately measuring and characterizing ciliary muscle activity, certain embodiments of the employ specialized electrode designs. For example, multiple bipolar electrodes may be used. Such electrodes can be segmented or multi-faceted, and may include, for example, one side of an electrode ring located outside a perimeter or circumference of the ciliary muscle and the opposite side electrode inside the perimeter or circumference of the ciliary muscle. This configuration may be used to cancel signals and/or reduce the overall signal magnitude.

In addition, certain embodiments may divide the electrode into segments or individual components in order to generate a more comprehensive map of the ciliary electrical activity. In such examples, different areas can be selected or disregarded (either manually by a care provider or automatically by a computer 606) as appropriate (e.g., based on alignment and position with respect to the perimeter or circumference of the ciliary muscle) to better characterize the true electrical signal (i.e., to obtain an accurate measurement of the electrical activity resulting from ciliary muscle movement).

For instance, each individual electrode segment of an electrode contact lens may be connected to an ophthalmic diagnostic system (e.g., computer 606) that includes a processor and memory configured to receive, process, and display (e.g., via display 608) a measure of detected ciliary muscle activity. A care provider may inspect an alignment of various electrode segments with the patient's ciliary muscle to identify and select the appropriate segments (e.g., those which are best aligned with the ciliary muscle) on which to base an evaluation, as described by step 104. In other examples, the diagnostic system automatically select the appropriate segments on which to base the evaluation. In different implementations, each segment may be continuously sampled or intermittently samples using a time-based multiplexing technique. One or more of these features may be used to optimize signal characterization and account for variables such as external lens movement, ciliary muscle movement with accommodation, and differences in ocular anatomy where otherwise the misaligned signal from one side could degrade the opposite side as the electrode position changes.

FIGS. 2A and 2B illustrate an example of a contact lens with two embedded circular electrodes for measuring ciliary muscle activity and illustrating principles of the present disclosure. Eye 200 comprises a ciliary muscle 202 indicated by a circle around the iris (not labeled). A transparent contact lens placed on the cornea of eye 200 comprises a reference electrode 204 and a measurement electrode 206. Measurement electrode 206 sized to overlay the perimeter of ciliary muscle 202, while reference electrode 204 is larger and lies further away from ciliary muscle 202, outside the circumference. (In alternative embodiments, reference electrode 204 could be smaller than measurement electrode 206, lying further away from ciliary body 202 but closer to the pupil of eye 200.) The difference in an electrical signal received from reference electrode 204 and measurement electrode 206 can be used to measure the magnitude of electrical signal in ciliary body 202. In a well-aligned example, as shown in FIG. 2A, the difference in signal strength between reference electrode 204 and measurement electrode 206 will be the same or similar at any angle. For example, the signal difference left of the pupil of eye 200 would be the same as the signal difference to the right of the pupil, or above or below it as well. In certain examples, the measured signal (over 360 degrees) may be determined by summing these differences across all angles.

FIG. 2B illustrates the same features of FIG. 2A, but with reference electrode 204 and measurement electrode 206 misaligned superiorly with respect to ciliary muscle 202. In this example, reference electrode 206 is positioned over ciliary muscle 202, inferiorly and the difference signal (between reference electrode 204 and measurement electrode 206) in this position could dramatically depart from the analogous difference signal in the position showing in FIG. 2A. In some cases, the inferior signal measured in FIG. 2B (near the bottom of electrodes 204, 206) may be the inverse of that in FIG. 2A.

Superiorly, neither reference electrode 204 nor measurement electrode 206 is well-aligned to ciliary muscle 202, and the measured superior difference signal measured in FIG. 2B (near the top of electrodes 204, 206) may be very small. As a result, the measured signal over 360 degrees may differ significantly in FIG. 2B, compared with the measurement taken in the arrangement show in FIG. 2A. Although superior displacement is shown in this example, relative displacement between electrodes 204, 206 and ciliary body 202 could occur in any direction.

FIG. 3 illustrates an electrode arrangement for a ciliary-activity detecting contact lens which can help overcome difficulties caused by displacement, according to certain embodiments. In particular, lens 300 comprises four concentric electrode rings 301-304, each divided into four segments shown as groups 310, 312, 314, and 316. Outer ring electrode 304 and each smaller ring 302, 303, and 304 can each measure electrical activity in each segment 310, 312, 314, and 316, providing a reading at sixteen separate segments or channels. Although a total of sixteen segments or channels is shown in FIG. 3, the number of rings and their division may be varied as appropriate to optimize performance while managing complexity, as an increasing number of channels requires increasing complexity in electrical design and processing requirements. For example, certain embodiments may include between two and six concentric electrode rings divided into between two and six groups, thereby providing anywhere between 4 and 36 segments or channels. Other variations are contemplated within the scope of the present disclosure.

Notably, the present disclosure is not limited to an electrode configuration of segmented annuli as shown in FIG. 3. Other embodiments may include a lens having differently shaped, sized, or arranged electrodes. FIG. 4, for example, illustrates an embodiment of a lens 400 which includes an outer ring of electrodes 410 and an inner ring of electrodes 420, each including sixteen electrode segments. Accordingly, the embodiment of FIG. 4 may support up to 32 channels. Again, although a total of 32 channels are shown in FIG. 4, the number of electrodes and rings may vary as appropriate to optimize performance while managing complexity, as an increasing number of channels requires increasing complexity in electrical design and processing requirements. For example, certain embodiments may include between two and six concentric electrode rings, each including between three and 20 electrodes, thereby providing anywhere between 6 and 120 channels. Other variations are contemplated within the scope of the present disclosure.

FIG. 5 illustrates possible scenarios resulting from application of a contact lens comprising electrode rings (identical to lens 300 shown in FIG. 4) to a patient. In FIG. 5A, lens 300 is centered on eye 200 and all four segments of the third ring from the center (corresponding to ring 303 of FIG. 3) are well-aligned with the perimeter or circumference of ciliary muscle 202. Summing the signals generated by each of the four segments of ring 303 yields a signal comparable to that obtained from measurement electrode 206 shown in FIG. 2A—a result that may be considered accurate and reliable.

In contrast, lens 300 of FIG. 5B is decentered (misaligned superiorly, analogous to FIG. 3B) on eye 200. As a result, the segments of ring 303 are not well-aligned to ciliary body 202 in FIG. 5B, and summing the signals generated by each of the four segments of ring 303 would yield a signal comparable to that obtained from measurement electrode 206 shown in FIG. 2B—likely an unreliable and inaccurate result.

However, in FIG. 5B, the lower electrodes of ring 304 (toward the bottom of FIG. 5B, corresponding to segments 314 and 316 shown in FIG. 3) are well-aligned to ciliary body 202. Similarly, the upper electrodes of ring 302 (toward the top of FIG. 5B, corresponding to segments 310 and 312 shown in FIG. 3) are suitably aligned to ciliary body 202. As a result, summing the signals generated by the two lower electrodes of ring 304 and two upper electrodes of ring 302 yields a result comparable to that obtained from measurement electrode 206 shown in FIG. 2A—again, a result that may be considered accurate and reliable.

In this manner, a lens comprising a plurality of electrode segments configured to independently generate and transmit signals may be used to accurately evaluate ciliary muscle activity in accordance with the method of FIG. 1, even if the lens is misaligned with respect to the ciliary body. This can be achieved by selecting signals from electrodes which are well-aligned with the ciliary muscle. Such a selection may be performed manually by a care provider, or automatically by a computer 606, as discussed below.

Figure 6:
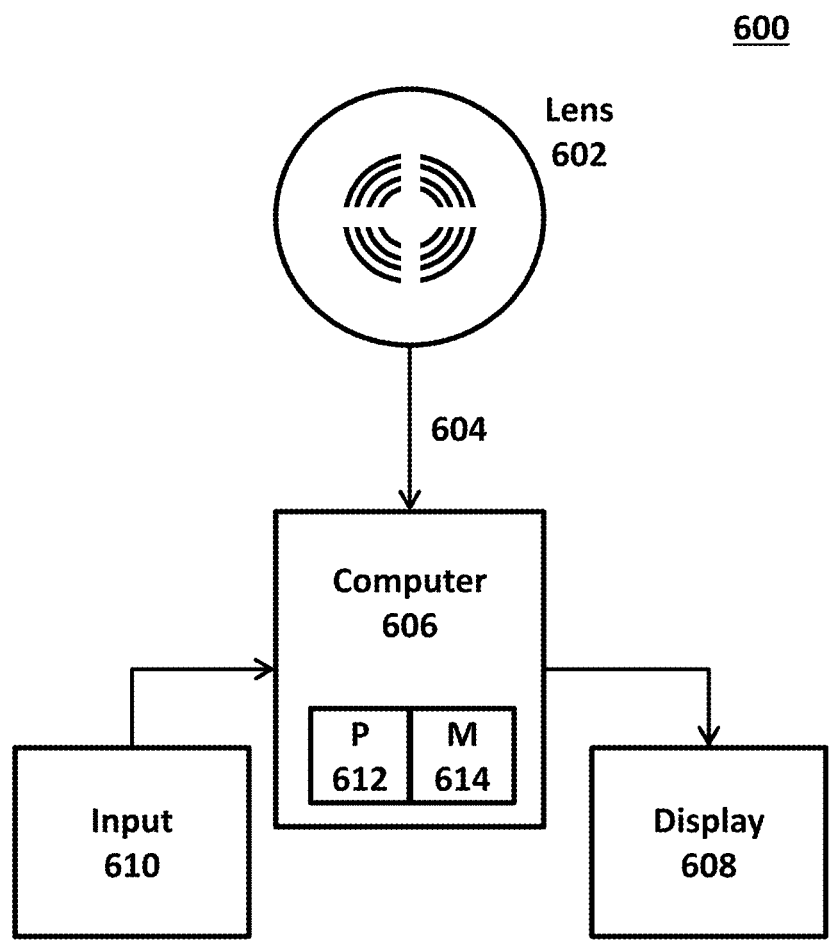
FIG. 6 illustrates an ophthalmic system, according to certain embodiments.

FIG. 6 illustrates an ophthalmic system 600 which may be used to perform method 100, according to certain embodiments. The system includes one or more electrode contact lenses 602 are designed for placement on the surface of the cornea of a patient's eye for a ciliary muscle evaluation procedure. Lens 602 may comprise multiple electrodes and segments as shown in FIGS. 3 and 5, but is not limited to the arrangement shown in those embodiments.

Once lens 602 is placed on a patient's eye, a care provider may perform the steps illustrated and described above with respect to step 102 of FIG. 1. In some instances, as the patient looks at objects at varying distances, the ciliary muscle attempts to change the focusing power of the natural lens accordingly. This causes a change in the electrical field of the patient's ciliary muscle(s). At each distance, electrical signals 604 generated by each electrode or channel of lens 602 may be transmitted to and received by a computer 606 which includes a processor and memory configured to execute instructions for processing the signals 604. Signals 604 may be transmitted to computer 606 via wired or wireless communication. In certain embodiments, particular segments or channels of the multi-electrode lens 602 aligned with the patient's ciliary body may be identified and selected by computer 606, as discussed above with respect to the example of FIG. 5B.

Computer 606 comprises one or more processors 612 and memory 614. Memory 614 may include persistent and volatile media, fixed and removable media, and magnetic and semiconductor media. Memory 614 is operable to store programs, codes, scripts, instructions, data, and the like. Memory 614 as shown includes sets or sequences of instructions, namely, an operating system, and an ophthalmic diagnostic program. The operating system may be a UNIX or UNIX-like operating system, a Windows® family operating system, an Apple® family operating system (e.g., macOS, iOS), or another suitable operating system. Instructions and data stored in memory 614 are accessible to processor 612 and are executable by the processor 612 to perform the steps discussed herein. The processor 612 may be or include a general purpose microprocessor, as well as a specialized co-processor or another type of data processing apparatus. In some cases, the processor 612 performs high level operation of the ciliary function diagnostic evaluation discussed herein. The processor 612 may be configured to execute or interpret software, scripts, programs, functions, executables, or other instructions stored in the memory 614 to receive, interpret, process, and evaluate signals generated by electrodes during ciliary muscle screening (e.g., as described in the process 100 of FIG. 1). Accordingly, computer 606 is specially adapted to perform ophthalmic-specific processes related to ciliary muscle function, as described herein.

For example, a processor of computer 606 may execute instructions to compare and evaluate signals 604 received from each electrode or channel of lens 602 to determine and select the best signals for further processing and/or evaluation. In certain examples, the processor of computer 604 may execute summing, averaging, comparing, and/or statistical processing algorithms using the received signals to identify and select a subset of signals which provide the most accurate and/or reliable indication of ciliary muscle activity. In some examples, this may include identifying and selecting signals which, based on the algorithm performed by the processor, are best situated within and aligned to the perimeter or circumference of the ciliary muscle. Algorithms executed by the processor may include also comparing each received signal with upper and lower thresholds, mean or median values (which may be calculated based on received signals), or other indicia useful for evaluating the quality and/or reliability of the received signal. As noted above, the subset of electrode signals selected may depend on the position of the contact lens on the patient's eye, as well as the characteristics of the patient's eye itself.

Additionally or alternatively, the instructions can be encoded as pre-programmed or re-programmable logic circuits, logic gates, or other types of hardware or firmware components.

In some examples, a user may use an input device 610 (e.g., keyboard, mouse, touch screen, voice recognition, etc.) to assist with the identification and selection of particular segments or channels of the multi-electrode lens 602 for the evaluation step. Additionally or alternatively, computer 606 may identify and select particular segments or channels of the multi-electrode lens 602 for the evaluation step automatically, based on algorithms noted above.

Additionally, the processor of computer 606 may execute instructions to process raw signal data and convert them to numerical values or other measurements which characterize ciliary muscle activity, responsiveness, strength, and/or accommodative capacity. Raw or processed signal data may be output by the computer and shown on a display 608 (e.g., a monitor, screen, heads-up display, tablet device, etc.). Based on the displayed data and information, the care provider may then proceed to step 104 and evaluate the results and data obtained from multi-electrode lens 602. Additionally or alternatively, the processor of computer 606 may compare the selected measurement values and data to predetermined thresholds, targets, and ranges to provide a notification, recommendation, or alert to the care provider via display 608.

It is noted that the processor of computer 606 may include one or more CPUs, microprocessors, field-programmable gate arrays (FPGAs), application-specific integrated circuits (ASICs), digital-signal processors (DSPs), system-on-chip (SoC) processors, or analogous components. The memory of computer 606 may include volatile or non-volatile memory including, magnetic media, optical media, random access memory (RAM), read-only memory (ROM), removable media, or analogous components. The memory of computer 606 may store instructions for software programs and algorithms that, when executed by the processor, analyze signals received from lens 602 as discussed above. As used in the claims, the terms "processor," "memory," "instructions," and the like refer to classes of structures that are well-known to those skilled in the art. As such, these terms are to be understood as denoting structural rather than functional elements of the disclosed system.

Accordingly, embodiments of the present disclosure provide novel and useful systems and methods for preoperatively assessing a patient's ciliary electrical activity. Using the disclosed systems and methods, a care provider may identify eyes in which a ciliary muscle-driven accommodative ophthalmic device would not function as intended, prior to surgery or purchase, to guide the decision on whether such devices are appropriate for a particular individual. Conversely, using the disclosed systems and methods, a care provider may identify eyes in which a ciliary muscle-driven accommodative ophthalmic device would likely function well, prior to surgery or purchase, to guide the decision on whether such devices are appropriate for a particular individual.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method, comprising:
   receiving a plurality of signals generated by a plurality of bipolar electrodes in response to ciliary muscle activity, the plurality of bipolar electrodes comprising a plurality of concentric rings, wherein each of the plurality of concentric rings comprises a plurality of segments, each of the plurality of signals indicating an electrical field associated with a patient's ciliary muscle; and
   analyzing the received signals to evaluate the ciliary muscle accommodative potential, wherein analyzing the signals comprises:
      identifying a subset of signals which correspond to a subset of the pluralities of segments of the concentric rings aligned with the ciliary muscle, and
      calculating a value associated with the identified subset of the pluralities of segments, wherein calculating the value comprises summing a first signal of the subset of signals generated by at least one segment of a first concentric ring and a second signal of the subset of signals generated by at least one segment of a second concentric ring.

2. The method of claim 1, further comprising:
   providing a contact lens to be applied to the patient's eye, the contact lens comprising the plurality of bipolar electrodes.

3. The method of claim 1, wherein evaluating the ciliary muscle accommodative potential based on the calculated value comprises comparing the calculated sum of the identified subset of signals to a predetermined value.

4. The method of claim 1, wherein evaluating the ciliary muscle accommodative potential comprises detecting changes in the plurality of signals received, as the ciliary muscle changes the focusing power to focus on one or more targets at different distances.

5. The method of claim 1, wherein the plurality of concentric rings comprises at least three concentric rings.

6. The method of claim 1, wherein the plurality of concentric rings comprises four concentric rings.

7. An ophthalmic system, comprising:
   a contact lens configured to contact a surface of a patient's eye, the contact lens comprising a plurality of bipolar electrodes comprising a plurality of concentric rings, wherein each concentric ring comprises a plurality of segments, each of the plurality of segments configured to generate a signal indicating an electrical field associated with a patient's ciliary muscle; and
   one or more processors and a memory comprising instructions that are operable, when executed by the one or processors, to:
      receive a plurality of signals generated by the pluralities of segments of the concentric rings during a ciliary muscle assessment procedure, each of the plurality of signals indicating an electrical field associated with the patient's ciliary muscle;
      analyze the received signals to identify a subset of signals that provide accurate measurement of the electrical activity from the ciliary muscle, wherein the subset of signals are received from a subset of the pluralities of segments of the concentric rings aligned with the patient's ciliary body; and
      calculate a value associated with the identified subset of the pluralities of segments; and
   a display communicatively coupled to the processor and configured to display the calculated value associated with the identified subset of the pluralities of segments.

8. The system of claim 7, wherein calculating the value associated with the identified subset of the pluralities of segments comprises summing a first signal of the subset of signals generated by at least one segment of a first concentric ring and a second signal of the subset of signals generated by at least one segment of a second concentric ring, wherein the first and second concentric rings are adjacent rings of the plurality of concentric rings.

9. The system of claim 8, wherein the instructions are operable, when executed by the one or more processors, to compare the calculated sum of the selected subset of signals to a predetermined value.

10. The system of claim 7, wherein the plurality of concentric rings comprises at least three concentric rings.

11. The system of claim 7, wherein the plurality of concentric rings comprises four concentric rings.

* * * * *